(12) United States Patent
Andersen et al.

(10) Patent No.: US 12,279,893 B2
(45) Date of Patent: Apr. 22, 2025

(54) METHOD AND SYSTEM FOR FILTERING NOISE OF AN IMPLANTABLE MEDICAL DEVICE

(71) Applicant: Pacesetter, Inc., Sylmar, CA (US)

(72) Inventors: Dean P. Andersen, San Jose, CA (US); Christopher Gloschat, Salt Lake City, UT (US)

(73) Assignee: Pacesetter, Inc., Sylmar, CA (US)

( * ) Notice: Subject to any disclaimer, the term of this patent is extended or adjusted under 35 U.S.C. 154(b) by 414 days.

(21) Appl. No.: 17/076,327

(22) Filed: Oct. 21, 2020

(65) Prior Publication Data

US 2022/0117560 A1    Apr. 21, 2022

(51) Int. Cl.
*A61B 5/00* (2006.01)
*A61B 5/349* (2021.01)
*A61N 1/362* (2006.01)

(52) U.S. Cl.
CPC ............ *A61B 5/7214* (2013.01); *A61B 5/349* (2021.01); *A61N 1/3627* (2013.01)

(58) Field of Classification Search
CPC ....... A61B 5/7267; A61B 5/7203; A61B 5/30; A61B 2560/0223; A61B 5/7271; A61B 5/725; A61B 2018/00839; A61B 5/0031; A61B 5/02; A61B 5/4836; A61B 5/304; A61B 5/486; G16H 50/20; A61N 1/3702; A61N 1/3704; A61N 1/025
See application file for complete search history.

(56) References Cited

U.S. PATENT DOCUMENTS

| | | | | |
|---|---|---|---|---|
| 8,725,238 B2 * | 5/2014 | Liu | ......................... | A61B 5/726 600/509 |
| 9,320,470 B2 * | 4/2016 | Keenan | ................. | A61B 5/7203 |
| 2019/0114393 A1 * | 4/2019 | Andersen | ............. | A61N 1/3702 |

OTHER PUBLICATIONS

Tereshchenko et al. "Frequency Content and Characteristics of Ventricular Conduction" J Electrocardiol. 2015 ; 48(6): 933-937. (9 pages).
Irnich "Electronic Security systems and Active Implantable Medical Devices" Journal of Pacing and Clinical Electrophysiology , vol. 25, No. 8, Aug. 2002 (24 pages).

* cited by examiner

*Primary Examiner* — Deborah L Malamud
(74) *Attorney, Agent, or Firm* — Dean D. Small; The Small Patent Law Group, LLC

(57) ABSTRACT

A system is provided that includes one or more electrodes configured to be implanted proximate to a sensing site, and a memory configured to store first and second sets of filter parameters that define first and second noise stop bands. The system also includes an implantable medical device (IMD) that has inputs configured to receive sensed signals, the sensed signals include frequency components associated with physiology activity and frequency components associated with noise. The IMD also includes a band-stop filter communicating with the sensing channel inputs. When executing program instructions, a processor switches the band-stop filter from the first set of filter parameters to the second set of filter parameters to shift from the first noise stop band to the second noise stop band based on the noise in the environment of the patient.

20 Claims, 11 Drawing Sheets

METHOD AND SYSTEM FOR FILTERING NOISE OF AN IMPLANTABLE MEDICAL DEVICE

BACKGROUND

Embodiments herein relate generally to implantable medical devices, and more particularly to methods and systems for filtering noise of an implantable medical device.

Implantable medical devices (IMD) include pacemakers, cardioverters, cardiac rhythm management devices, defibrillators, whether lead-based or leadless, or the like. Each product is implanted in an individual to treat heart ailments and conditions through an electronically operated device. Many implantable medical products store a large amount of biological data from sensors.

A variety of sensors, the most basic being electrical sensing of the heart, are constantly being monitored and stored in memory. Noise sources such as alternating current (AC) voltage sources can introduce noise that is close or in the band of frequencies that are of interest to signals that are being monitored. Such noise can cause incorrect signal interpretation and interfere with the general operation of the IMDs.

Filters are utilized to block this extrinsic noise from interfering with signal interpretation performed by the IMD. However, filters typically only block a single frequency, or a small range of frequencies. For example, for an IMD that is utilized by a patient in the United States, the filter may be set up to block 60 Hz frequencies, or in a range from 55 Hz to 65 Hz. Specifically, 60 Hz is the frequency provided by power outlets in a home or office for electrical devices to operate. Still, in other locations in the world, such as many countries in Europe, certain areas of Japan, etc. 50 Hz is the frequency provided by power outlets in homes and offices. As a result, when a patient from the United States travels to Europe, Japan, or one of these locations, the most common noise in the environment is 50 Hz, which would be outside the range of a fixed 60 Hz filter. Similarly, while 60 Hz is the frequency most common in the United States, in certain locations within the United States different frequencies other than 60 Hz or more common. As examples, hospitals equipment, industrial equipment and facilities, places such as shopping malls that use certain surveillance equipment, etc. all present different environments that can have noise outside the range of a fixed filter. In each instance, the noise interferes with the signal interpretation of the IMD, causing inaccuracies.

SUMMARY

In one or more embodiment, a system is provided that includes one or more electrodes configured to be implanted proximate to a sensing site, and a memory configured to store first and second sets of filter parameters that define first and second noise stop bands. The system also includes an implantable medical device (IMD) that has inputs configured to receive sensed signals from the one or more electrodes, the sensed signals include frequency components associated with physiology activity and frequency components associated with noise. The IMD also includes a band-stop filter communicating with the sensing channel inputs. The band-stop filter utilizes the first set of filter parameters to define upper and lower cut-off frequencies of the first noise stop band. The band-stop filter is also configured to pass the frequency components above and below the upper and lower cut-off frequencies associated with physiology activity, respectively, while at least partially block frequency components between the upper and lower cut-off frequencies associated with the noise. The IMD also includes a memory to store program instructions and a processor. When executing the program instructions, the processor is configured to at least one of analyze the physiologic signals or deliver a therapy, and switch the band-stop filter from the first set of filter parameters to the second set of filter parameters to change at least one of the upper and lower cut-off frequencies to shift from the first noise stop band to the second noise stop band.

Optionally, the system also includes an external device, wherein the processor is configured to wirelessly receive a filter change (FC) instruction from the external device. In response to the FC instruction, the processor is configured to manage the band-stop filter to switch from the first set of filter parameters to the second set of filter parameters. In one aspect, the external device (ED) comprises an ED transceiver, an ED processor and memory configured to store ED program instructions. The ED processor, when executing the ED program instructions is configured to determine a location of the external device and, based on the location. The ED processor is additionally configured to determine when to switch between the first and second sets of filter parameters. The ED transceiver is configured to wirelessly transmit the FC instruction to the IMD based on the determination.

Optionally, the processor is further configured to wirelessly receive the second set of filter parameters and, in connection there with, switch from the first set of filter parameters to the second set of filter parameters. In another aspect, the band-stop filter is implemented in firmware having registers configured to hold a current one of the first and second sets of filter parameters to define the upper and lower cut-off frequencies. The memory is configured to simultaneously store both the first and second sets of filter parameters, the band-stop filter configured to upload the second set of filter parameters into the registers of the firmware to shift to the second noise stop band. Alternatively, the memory further comprises software that defines the band-stop filter, and the processor configured to implement the software utilizing one of the first and second sets of filter parameters. In one example, the upper and lower cut-off frequencies are the same. Alternatively, the upper cut-off frequency is in a range between 45 Hz and 75 Hz and the lower cut-off frequency is also in a range between 45 Hz and 75 Hz.

Optionally, the ED is one of a workstation, a portable computer, an IMD programmer, a personal digital assistant (PDA), a phone, or a watch. In one aspect, the band-stop filter is a digital filter.

In one or more embodiments a method is provided for managing location based operations of an implantable medical device (IMD) in communication with an external device (ED). The method includes, under control of one or more processors, receiving, at inputs of the IMD, sensed signals from one or more electrodes configured to be implanted, the sensed signals include frequency components associated with physiology activity and frequency components associated with noise. The method also includes band-stop filtering, at the IMD, the sensed signals utilizing a first set of filter parameters that define upper and lower cut-off frequencies of a first noise stop band. The band-stop filtering also includes passing the frequency components above and below the upper and lower cut-off frequencies associated with physiology activity, respectively, while at least partially blocking frequency components between the upper and lower cut-off frequencies associated with the noise. The method also includes obtaining location information indicative of a location of at least one of the IMD or ED, and based on the location information, switching the band-stop filtering from the first set of filter parameters to a second set of filter parameters to change at least one of the upper and lower cut-off frequencies to shift from the first noise stop band to a second noise stop band.

Optionally, the location information is obtained by the ED, and the method also includes wirelessly transmitting a filter change (FC) instruction from the ED to the IMD. The method additionally includes, in response to the FC instruction, the IMD switching from the first set of filter parameters to the second set of filter parameters. In one aspect, based on the location information, the method includes determining when the location of the IMD has moved from a first location to a second location, wirelessly transmit the FC instruction to the IMD based on the determining. In another aspect the method also includes wirelessly transmitting the second set of filter parameters from the ED to the IMD, based on the location information and, in connection therewith, switching from the first set of filter parameters to the second set of filter parameters. In one example, the method additionally includes simultaneously storing both the first and second sets of filter parameters in memory of the IMD, and uploading the second set of filter parameters into registers of firmware of the IMD to shift to the second noise stop band.

Optionally, the method further includes monitoring movement from a first location to a second location. The switching the band-stop filtering from the first set of filter parameters to the second set of filter parameters to change at least one of the upper and lower cut-off frequencies to shift from the first noise stop band to the second noise stop band is based on the movement from the first location to the second location. In one aspect, the first set of filter parameters are in a range between 45 Hz and 55 Hz at the first location, and the second set of filter parameters are in a range between 55 Hz and 65 Hz at the second location. In another aspect, obtaining location information indicative of a location of at least one of the IMD or ED comprises obtaining a signal from a global positioning system of at least one of the IMD or ED. In one example, switching the band-stop filtering from the first set of filter parameters to the second set of filter parameters to change at least one of the upper and lower cut-off frequencies to shift from the first noise stop band to the second noise stop band is based on the location of the at least one of the IMD or ED being where electronic article surveillance equipment is present. In another example, switching the band-stop filtering from the first set of filter parameters to the second set of filter parameters to change at least one of the upper and lower cut-off frequencies to shift from the first noise stop band to the second noise stop band is based on the location of the at least one of the IMD or ED being where a welding device is present.

DETAILED DESCRIPTION

Figure 1:
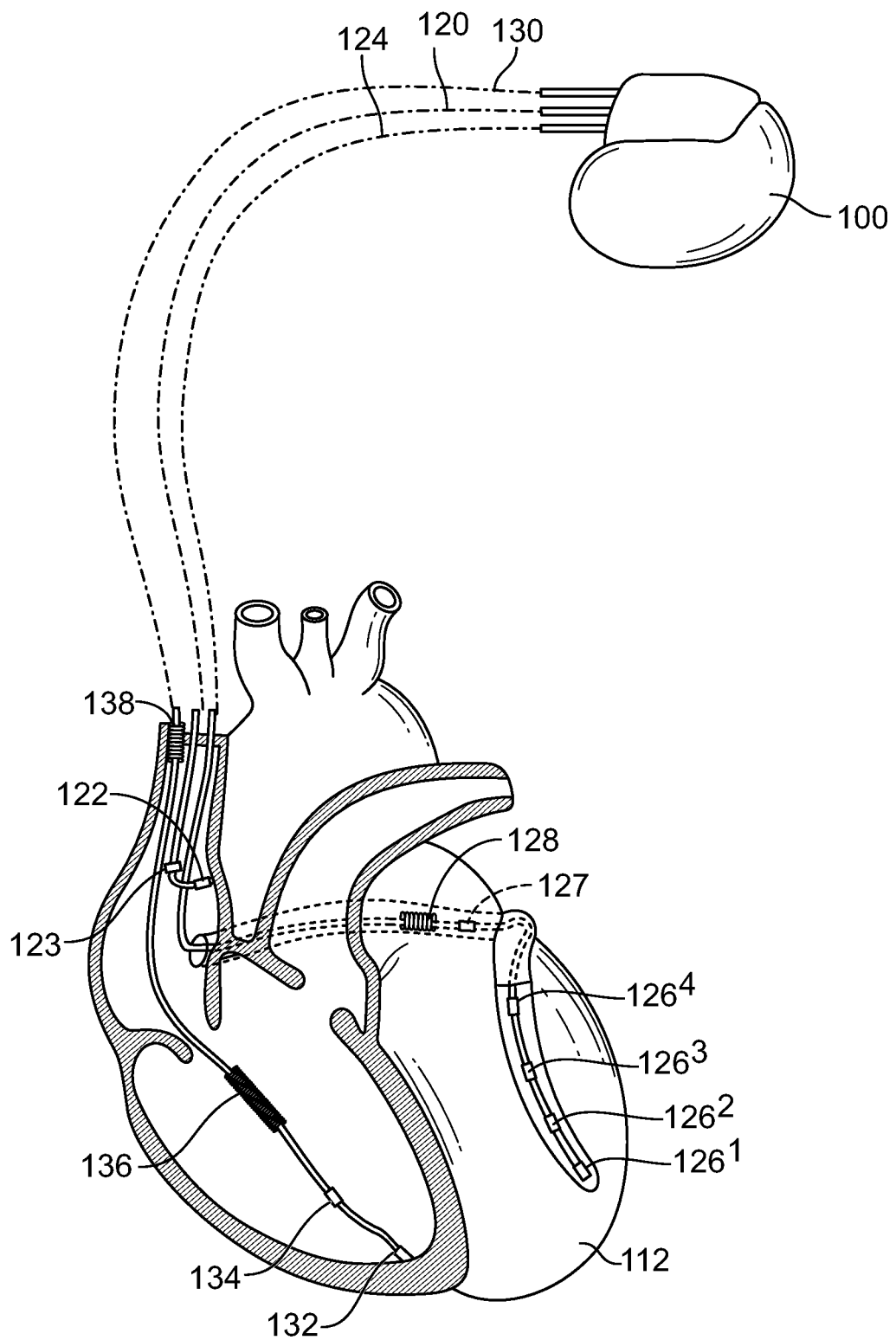
FIG. 1 illustrates an exemplary IMD formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "noise" refers to any and all disturbances in a communication signal. The communication may be electronic, wireless, over the air, through a cellular network, or the like. The noise may include any random error, deflection, etc. from the intended signal. Noise can be measured in units for frequency, energy, or the like.

The term "upper cut-off frequency" refers to the maximum frequency that is filtered by a filtering device such as a band-stop filter. Specifically, a band-stop filter can filter noise in a range, such as 5 Hz, 10 Hz, etc. where the maximum frequency is the upper cut-off frequency. In this manner, if a band-stop filter filters noise in a 10 Hz range between 55 Hz and 65 Hz, 65 Hz is considered the upper cut-off frequency. If a band pass filter filters noise in a 4 Hz range between 48 Hz and 52 Hz, 52 Hz is the upper cut-off frequency.

The term "lower cut-off frequency" refers to refers to the minimum frequency that is filtered by a filtering device such as a band-stop filter. Specifically, a band-stop filter can filter noise in a range, such as 5 Hz, 10 Hz, etc. where the minimum frequency is the lower cut-off frequency. In this manner, if a band-stop filter filters noise in a 10 Hz range between 55 Hz and 65 Hz, 55 Hz is considered the lower cut-off frequency. If a band-stop filter filters noise in a 4 Hz range between 48 Hz and 52 Hz, 48 Hz is the lower cut-off frequency.

The term "filter parameters" refers to the frequency at which a filtering device, such as a band-stop filter, filters noise. The filter parameters can include a specific frequency at which noise is being filtered, or a range or band of frequencies. In this manner, the filter parameters in examples can be 50 Hz, 60 Hz, 70 Hz, 100 Hz, in a range between 50 Hz to 60 Hz, in a range between 70 Hz and 80 Hz, etc.

Embodiments may be implemented in connection with one or more IMDs. Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s) described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

A system is provided for using the electronic noise in an environment of a patient to determine and switch filter parameters of a filter to reduce noise from exterior power sources in the environment. As used herein, switching and/or managing a filter parameter refers to a change in the filter parameters including direct changes or indirect changes to parameter sets. For example, the processor may write a new parameter set into registers in a band-stop, or notch, filter. Additionally or alternatively, hardware or other circuitry in the IMD may cause the new parameter set to be written to registers of firmware. Optionally, the new parameter set may be received by the transceiver and loaded into the registers of the firmware. A parameter set can provide a range of frequencies to be filtered that are defined by a range of frequencies that include an upper cut-off frequency, and a lower cut-off frequency. In such an example, the upper cut-off frequency and the lower cut-off frequency are considered the parameter set.

Specifically, depending on the environment of the IMD, different noise or interference is common. By using the internet of things (IoT), mobile and cellular phone based information such as network location, connectivity information, or the like, global positioning system information from a phone associated with the IMD, or the like, a filter parameter is determined based on the noise within a determined environment.

For example, the AC frequency of standard power supplies in the United States are 60 Hz, while the AC frequency of standard power supplies in Europe are 50 Hz. Meanwhile, in Japan, certain regions operate at 50 Hz, while other regions operate at 60 Hz. In one embodiment, the system of the IMD determines where a person is located such that a person traveling starts in a first location in Europe with a filter parameter for filtering 50 Hz frequency, then when arriving in a second location in the United States, the system based on determining the new location switches the filter to filter 60 Hz frequency. The location may be determined by a global navigation system, connecting to determined networks, Bluetooth beacon systems, radio frequency identification, QR code identification, or the like to pinpoint the location of the patient.

In other examples, a patient may perform a job that requires them to be around a determined frequency, such as an individual that uses a welding device such as a plasma or ultrasound welder. The system switches frequency of the filter parameters based on a determined timed period entered by the patient or clinician when working hours are occurring, or based on a determination the patient is located at work. In another example, a sensor is utilized to directly detect noise in an environment. This information is then passed to the IMD, facilitating environment specific decisions on processing features and modes. For example, if a certain noise is detected in an environment, a notch filter is enabled once the noise is identified. In particular, a 50 Hz or 60 Hz notch filter could be applied as part of a noise removal algorithm.

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the coronary sinus (CS) region via the CS ostium for positioning a distal electrode adjacent to the left ventricle and/or additional electrode(s) adjacent to the left atrium. An exemplary LV lead 124 is designed to receive atrial and ventricular cardiac signals and to deliver left ventricular pacing therapy using a set of four left ventricular electrodes $126_1$, $126_2$, $126_3$, and $126_4$ (thereby providing a quadripole lead), left atrial pacing therapy using at least a left atrial ring electrode 127, and shocking therapy using at least a left atrial coil electrode 128 implanted on or near the left atrium.

In accordance with embodiments herein, methods and devices are provided that utilize S1 heart sounds to determine therapeutic pacing of the IMD. Specifically, the methods and devices measure a first heart sound S1, such as utilizing a three-dimensional accelerometer in the IMD. In particular, the methods and devices are further configured to switch from the BiV pacing therapy to a left univentricular (LV only) pacing therapy that delivers pacing stimulation at one or more left ventricular sites and does not deliver any pacing stimulation to any right ventricular sites. Once the pacing therapy is determined, the system may determine the effects of different offsets during pacing on the S1 sound to determine the offset for pacing.

Implantable Medical Device

Figure 2A:
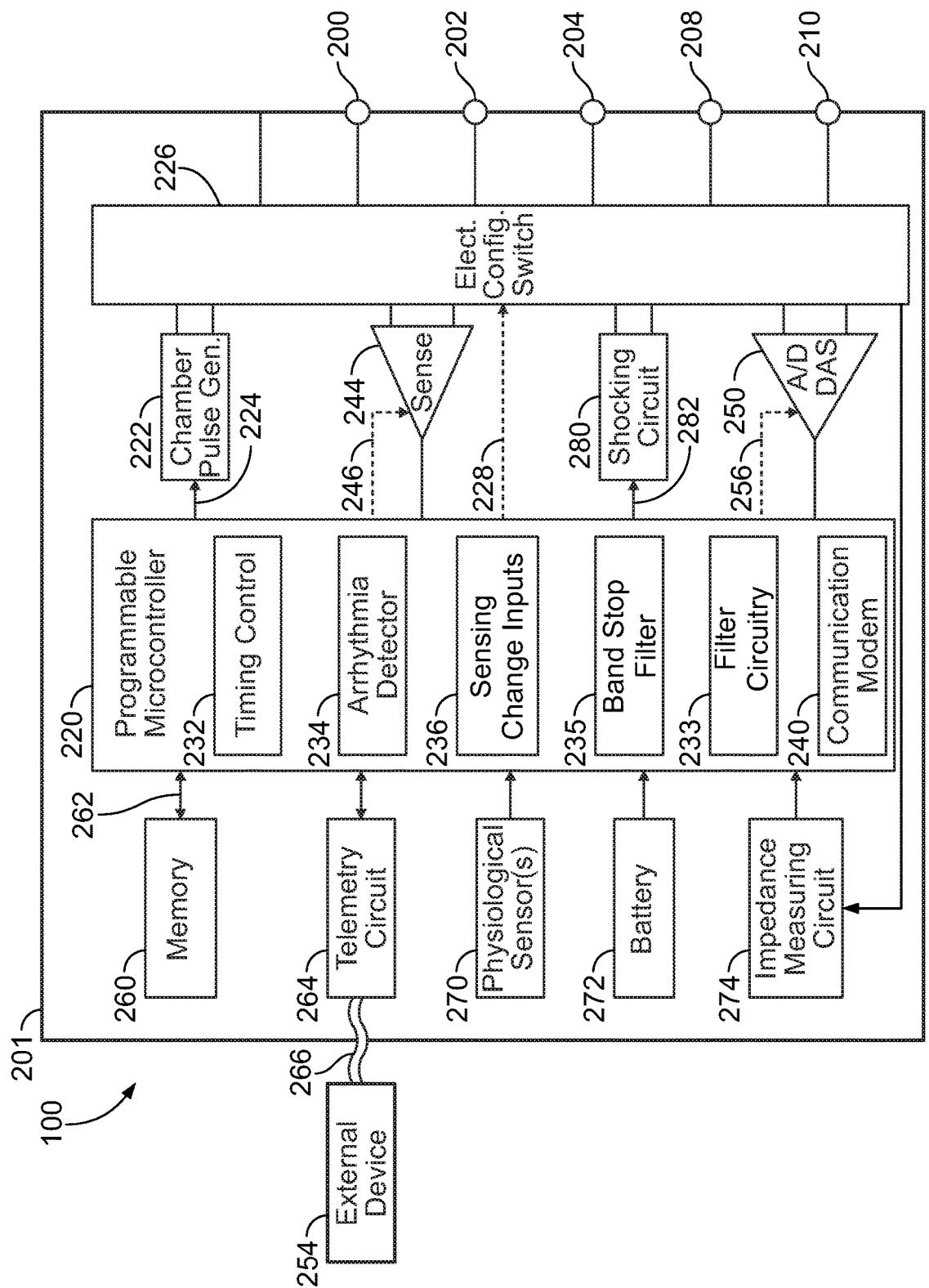
FIG. 2A shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components. For instance, the IMD may be implemented without ventricular sensing and pacing. As described herein, the IMD 100 is configured to provide LUV pacing therapy without pacing the RV.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals 202, 204, 206, 208, and 210. The terminals may be connected to electrodes that are located in various locations within and about the heart. For example, the terminals may include: a terminal 202 to be coupled to an first electrode (e.g., a tip electrode) located in a first chamber; a terminal 204 to be coupled to a second electrode (e.g., tip electrode) located in a second chamber; a terminal 206 to be coupled to an electrode (e.g., ring) located in the first chamber; a terminal 208 to be coupled to an electrode located (e.g., ring electrode) in the second chamber; and a terminal 210 to be coupled to an electrode (e.g., coil) located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. Microcontroller 220 includes a microprocessor (or equivalent control circuitry), RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

The microcontroller 220 includes filter circuitry 233 to implement the processes described herein for filtering noise. The filter circuitry 233 can be coupled to or receive communication signals from a band-stop filter 235 that in one example is a digital band-stop filter. In particular, the band-stop filter 235 communicates with sensing channel inputs 236 such that the band-stop filter 235 utilizes a first set of filter parameters to define upper and lower cut-off frequencies of a first noise stop band.

In one example, the first set of filter parameters include a frequency range between 48 Hz and 52 Hz where 48 Hz in the lower cut-off frequency and 52 Hz is the upper cut-off frequency. Such filter parameters may be indicative of a filter setting when the filter is located in a European country where the standard frequency for electronics is 50 Hz. In another example, the lower cut-off frequency and the upper cut-off frequency are the same, and both 50 Hz.

Figure 2B:
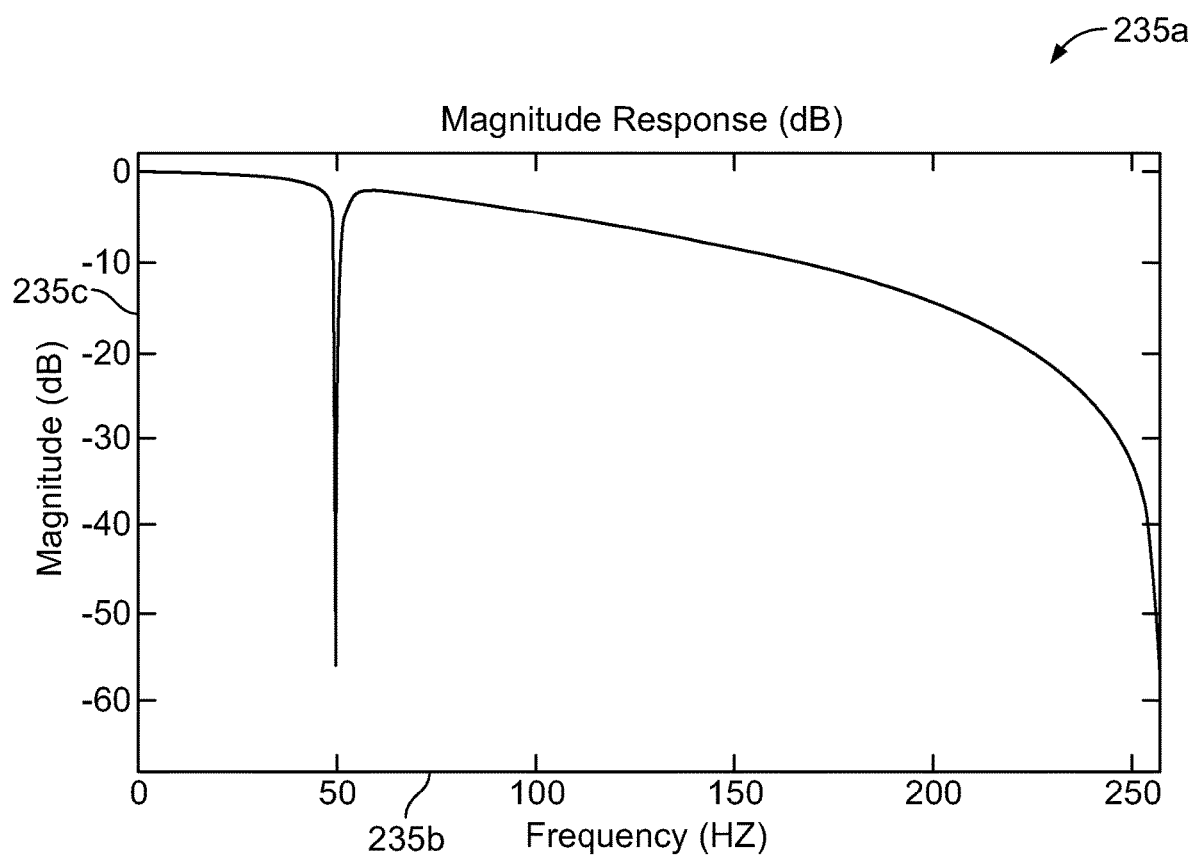
FIG. 2B illustrates a graph of a magnitude response of a filter in accordance with embodiments herein.

The band-stop filter 235 is configured to pass the frequency components above and below the upper and lower cut-off frequencies associated with physiology activity, respectively, while at least partially blocking frequency components between the upper and lower cut-off frequencies associated with the noise. In this manner, noise from 50 Hz electronic device is at least partially blocked. FIG. 2B illustrates a graph of a magnitude response 235a of a first order 50 HZ notch filter when measuring frequencies 235b in Hz over magnitude 235c in dB. As illustrated, frequencies at and in a range around 50 Hz between a lower cut-off frequency and an upper cut-off frequency are effectively blocked, preventing such noise form effecting results associated with the device utilizing the 50 Hz notch filter.

A band-stop filter switch 237 is also provided such that a processor of the microcontroller manages the band-stop filter to switch from the first set of filter parameters to a second set of filter parameters. In one example, the second set of filter parameters are between 58 Hz and 62 Hz where 58 Hz is the lower cut-off frequency and 62 Hz is the upper cut-off frequency. Again, in another embodiment the lower cut-off frequency and upper cut-off frequency are both 60 Hz. 60 Hz represents the frequency that electronic devices operate in the United States, and thus the band-stop filter filters noise created by these electronic devices by blocking 60 Hz frequencies. The band-stop filter switch 237 is provided to switch the band-stop filter from the first set of filter parameters to the second set of filter parameters. In one example, the band-stop filter switch 237 switches the band-stop filter from filtering 50 Hz frequencies to filtering 60 Hz frequencies.

In one embodiment, the band-stop filter 235 is implemented in firmware having registers configured to hold a current one of the first and second sets of filter parameters to define the upper and lower cut-off frequencies, and the memory of the microcontroller 220 is configured to simultaneously store both the first and second sets of filter parameters. The band-stop filter 235 is configured to upload the second set of filter parameters into the registers of the firmware to shift to the second noise stop band. The memory of the microcontroller 220 can also include software that defines the band-stop filter 235. Specifically, the processor of the microcontroller is configured to implement the software utilizing one of the first and second sets of filter parameters.

The IMD 100 is further equipped with a communication modem (modulator/demodulator) 240 to enable wireless communication with other devices, implanted devices, and/or external devices. The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuit 244 selectively coupled to one or more electrodes that perform sensing operations, through the switch 226 to detect the presence of cardiac activity in the right chambers of the heart. The sensing circuit 244 may include dedicated sense amplifiers, multiplexed amplifiers, or shared amplifiers. The output of the sensing circuit 244 is connected to the microcontroller 220 which, in turn, triggers or inhibits the pulse generator 222 in response to the absence or presence of cardiac activity. The sensing circuit 244 receives a control signal 246 from the microcontroller 220 for purposes of controlling the gain, threshold, polarization charge removal circuitry (not shown), and the timing of any blocking circuitry (not shown) coupled to the inputs of the sensing circuit.

The IMD 100 further includes an analog-to-digital (ND) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The memory 260 may be configured to include patient data, including whether a patient has LBBB. In particular, the control circuitry can determine if a patient has LBBB or can obtain the patient data from the memory.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity. Signals generated by the physiological sensors 270 are passed to the microcontroller 220 for analysis. The microcontroller 220 responds by adjusting the various pacing parameters (such as rate, AV Delay, VV Delay, etc.) at which the atrial and ventricular pacing pulses are administered.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The IMD 100 further includes an impedance measuring circuit 274 that is enabled by the microcontroller 220 via a control signal 282.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282.

Figure 3A:
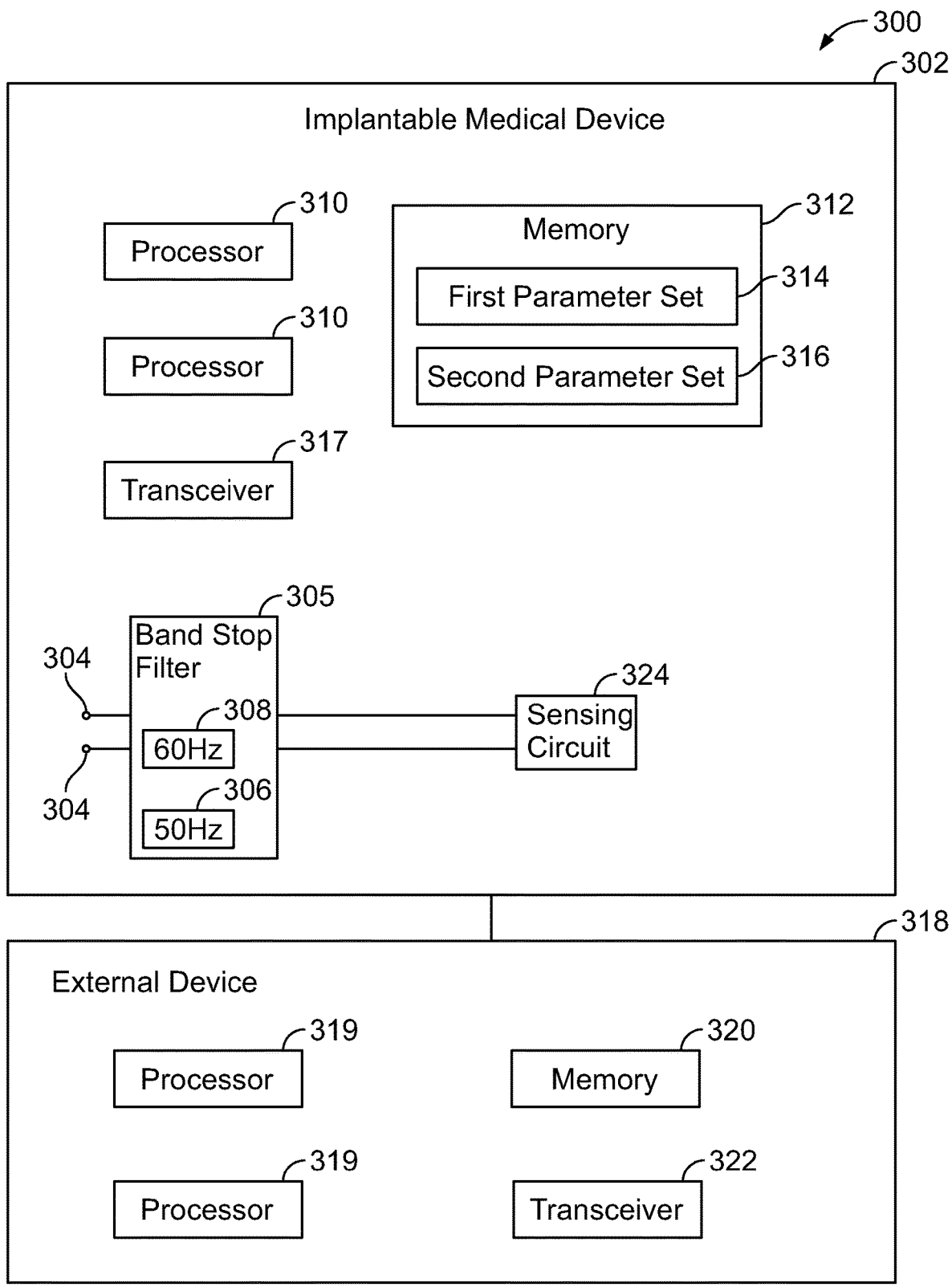
FIG. 3A illustrates a schematic diagram of a filter of an IMD, in accordance with embodiment herein.

FIG. 3A illustrates an example system 300 of an IMD 302. The system 300 includes inputs 304 that in one example are terminals. The inputs 304 receive sensed signals from one or more electrodes configured to be implanted. In one example, the electrodes are those as described in relation to FIGS. 1-2. The sensed signals include frequency components associated with physiology activity and frequency components associated with noise. In one example, the frequency components associated with physiology activity is related to heart signals monitored by the IMD 302. Meanwhile the frequency components associated with the noise include electronic signals from one or more EDs not primarily associated with obtaining physiology activity data for the IMD. For example, to be primarily associated with obtaining physiology activity for the IMD, the main purpose of the ED is to provide the physiology activity for the IMD. To this end, a smart watch that provides pulse information, or a computing device that stores and communicates patient physiology activity information for numerous patients, or functions as a patient's personal computer are neither primarily associated with obtaining physiology activity data for the IMD. Such EDs can include cell phones, electrical equipment, MRIs, welding devices, industrial machinery, computing devices, electrical towers, home appliances, surveillance equipment, etc.

The system 300 includes a filter 305 that receives signals from the inputs 304, and functions to block the frequency components associated with noise. In one embodiment, the filter 305 is a band-stop filter that includes filtering at a plurality of frequencies. In one example, the band-stop filter is a digital filter. In another example, the band-stop filter may include both a 50 Hz filter component 306 and a 60 Hz filter component 308. Alternatively, the filter components may be at different frequencies including 30 Hz, 40 Hz, 55 Hz, 70 Hz, or the like. In addition, the band-stop filter may include additional components that filter at different frequencies. In yet another embodiment, the filter components filter a range of frequencies such as 48 Hz to 52 Hz, 50 Hz to 60 Hz, 58

Hz to 62 Hz, etc. In particular, the filter 305 can have a first set of filter parameters that define upper and lower cut-off frequencies of a first noise stop band, and a second set of filter parameters that define a different upper and lower cut-off frequencies of a second noise stop band. The filter 305 is configured to pass frequency components above and below the upper and lower cut-off frequencies that are associated with physiology activity while at least partially blocking frequency components between the upper and lower cut-off frequencies associated with the noise.

The first set of filter parameters can be 50 Hz, with 50 Hz being the upper and lower cut-off frequencies; 48 Hz to 52 Hz, with 52 Hz being the upper cut-off frequency and 48 Hz being the lower cut-off frequency; 55 Hz to 65 Hz with 65 Hz being the upper cut-off frequency and 55 Hz being the lower cut-off frequency, etc. The second set of filter parameters can provide similar frequencies and frequency ranges as the first set of filter parameters, but is different than the first set of filter parameters.

The IMD 302 of the system 300 also includes one or more processors 310, and a memory 312 that contains at least a first set of filter parameters 314 and a second set of filter parameters 316, and a transceiver 317. The memory 312 may include additional sets of filter parameters. The filter 305 utilizes the sets of filter parameters based on the environment of the patient. Specifically, the system 300 is coupled to an ED 318 that includes one or more processors 319, a memory 320, and a transceiver 322. In one embodiment, the ED 318 can be a cell or mobile phone, monitoring equipment, personal computer, PDA, smart watch, etc. The ED 318 determines the environment of the patient and communicates a filter change (FC) instruction to the system 300. In one example, the FC instruction is communicated wirelessly from the ED 318 to the IMD 302. The IMD 302 then receives the FC instruction from the ED 318, and in response to the FC instruction, one or more processors of the system manage the filter 305 to switch from a first set of filter parameters to a second set of filter parameters. In this manner, the ED 318 may monitor or determine the electrical environment of the patient utilizing the methods and systems described herein, and provide the FC instruction to switch between different parameter sets to filter the frequency component associated with noise that is most likely to be present within the environment of the patient.

The system 300 also includes a sensing circuit 324 that receives filtered signals from the filter 305. After the filter 305 has been switched to provide the set of filter parameters selected for the environment of the patient, the signals from the inputs 304 are filtered by the filter 305 using the selected set of filter parameters and received by the sensing circuit 324 for analysis. By switching the filter parameters of the filter 305, improved and more accurate results are achieved by the IMD 302.

Figure 3B:
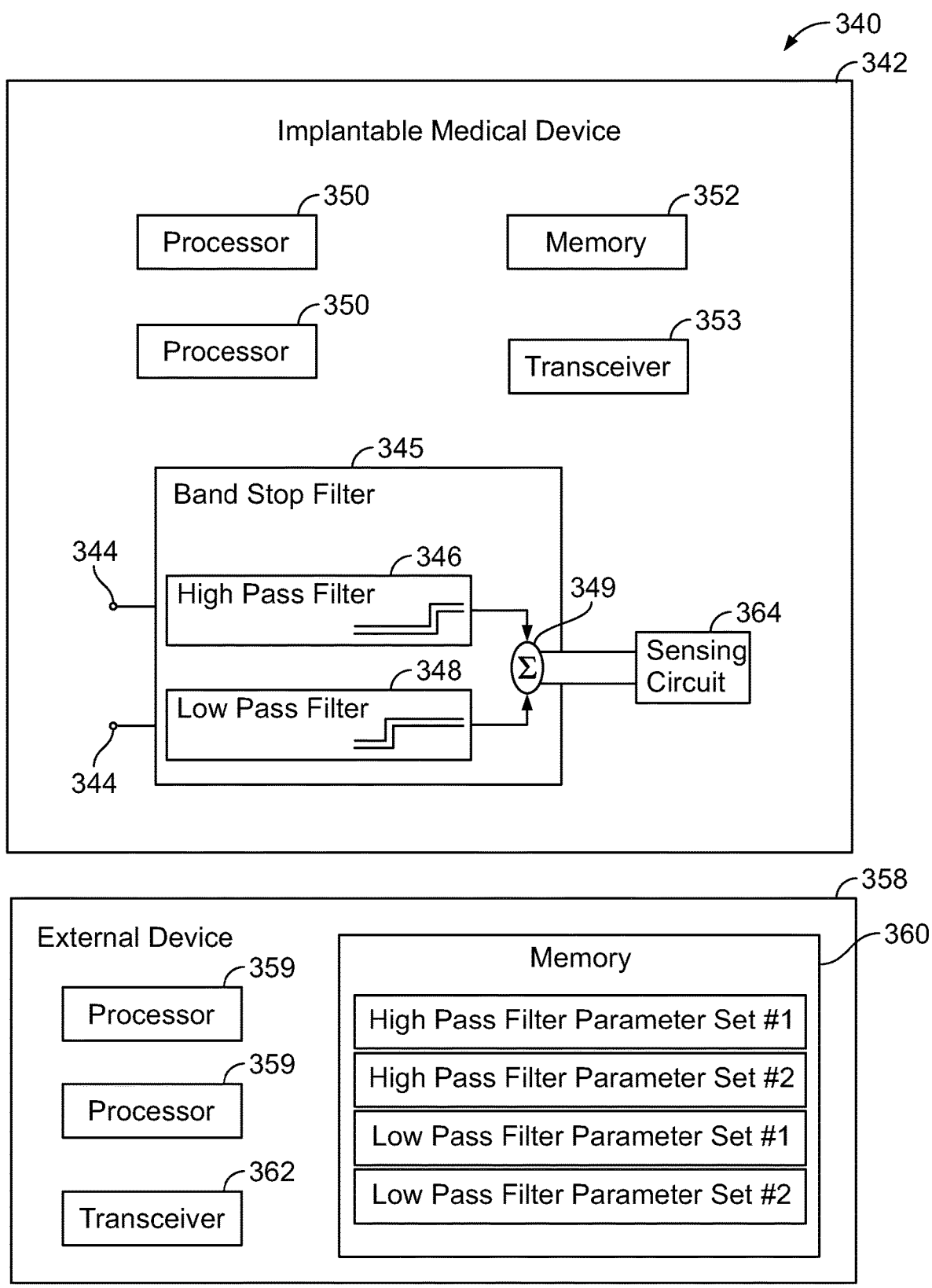
FIG. 3B illustrates a schematic diagram of a filter of an IMD, in accordance with embodiments herein.

FIG. 3B illustrates another embodiment of a system 340 that filters signals before analysis of the signals by an IMD 342. In this embodiment, the memory that stores the sets of filter parameters is associated with an ED instead of the IMD 342, and the filter includes a high-pass filter component and a low-pass filter component. The system 340 includes inputs 344 similar to the example system of FIG. 3A. A filter 345 then receives signals from the inputs 344. In one embodiment, the filter 345 is a band-stop filter. In one example, the band-stop filter is a digital filter.

In one embodiment, the filter 345 includes a high-pass filter component 346 and a low-pass filter component 348 that are then combined at a summation device 349. The high-pass filter component 346 functions to provide an upper cut-off frequency such that the high-pass filter only passes frequencies below the upper cut-off frequency. Similarly, the low-pass filter component 348 functions to provide a lower cut-off frequency such that the low pass filter only passes frequencies above the lower cut-off frequency. In one example, the summation device 349 is an op-amp circuit, and the high-pass filter component 346 and low-pass filter component 348 at least partially block noise frequencies between the upper cut-off frequency and lower cut-off frequency when the signals are summed.

The IMD 302 includes one or more processors 350, a memory 352, and a transceiver 353 that is in communication with an ED 358. The ED 358 can be a cell or mobile phone, monitoring equipment, personal computer, PDA, smart watch, etc. The ED 358 includes one or more processors 359, a memory 360, and a transceiver 362. In one embodiment, the memory 360 of the ED 358 includes a first set of filter parameters and a second set of filter parameters where the first and second set of filter parameters are utilized by the high-pass filter component 346 and low-pass filter component 348 to provide the upper cut-off frequency and the lower cut-off frequency. The ED 358 determines the environment of the patient, and based on the environment determines a set of filter parameters to communicate to the high-pass filter element 346 and the low-pass filter element 348. The ED 358 then communicates a FC instruction to the IMD 302 that includes a first set of filter parameters, second set of filter parameters, third set of filter parameters, etc. based on the environment of the patient.

The system 300 also includes a sensing circuit 364 that receives a filtered signal from the filter 345. After the filter has been switched to provide the set of filter parameters selected for the environment of the patient, the signals from the inputs 344 are filtered by the filter 345 and received by the sensing circuit 364 for analysis. By switching the filter 345, improved and more accurate are achieved by the IMD 302.

Figure 3C:
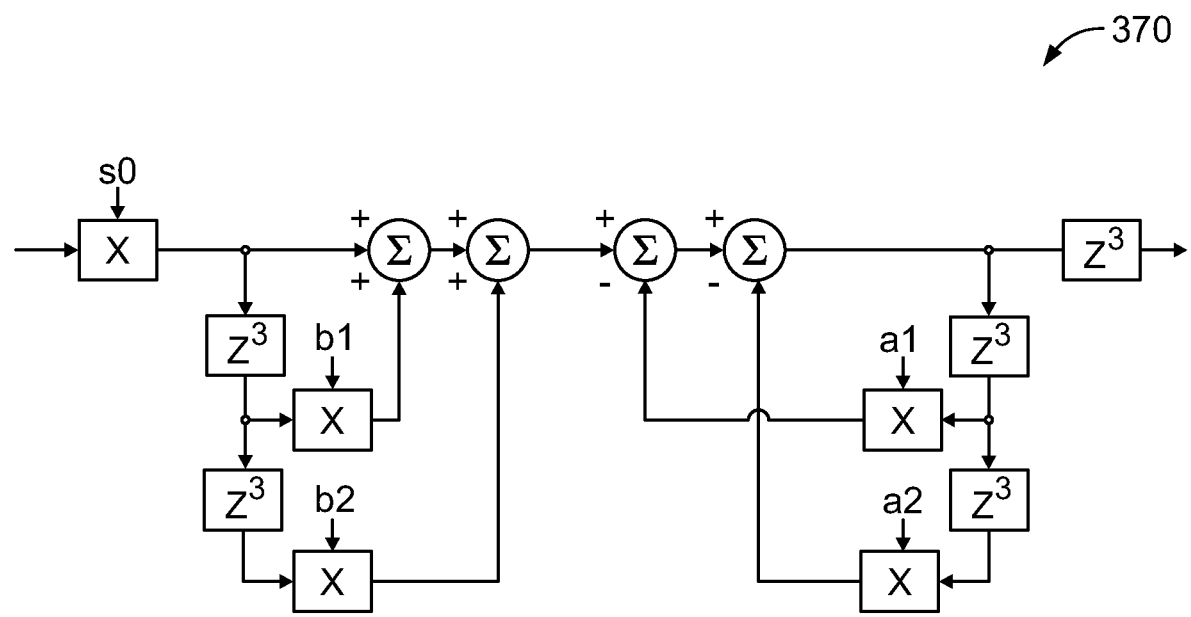
FIG. 3C illustrates a schematic diagram of a filter of an IMD, in accordance with embodiments herein.

FIG. 3C illustrates a digital filter 370 that is used in at least one embodiment of the systems described in FIGS. 1-3B. In one example, the digital filter 370 is a biquad filter section. The digital filter 370 is programable and can implement a variety of filtering functions. Specifically, the digital filter 370 can function as a first order 50 Hz filter, or a first order 60 Hz band-stop filter by changing coefficient values b1, b2, a2, and a3. In this manner, the digital filter 370 is a type I second order infinite pulse response (IIR) filter.

Figure 4:
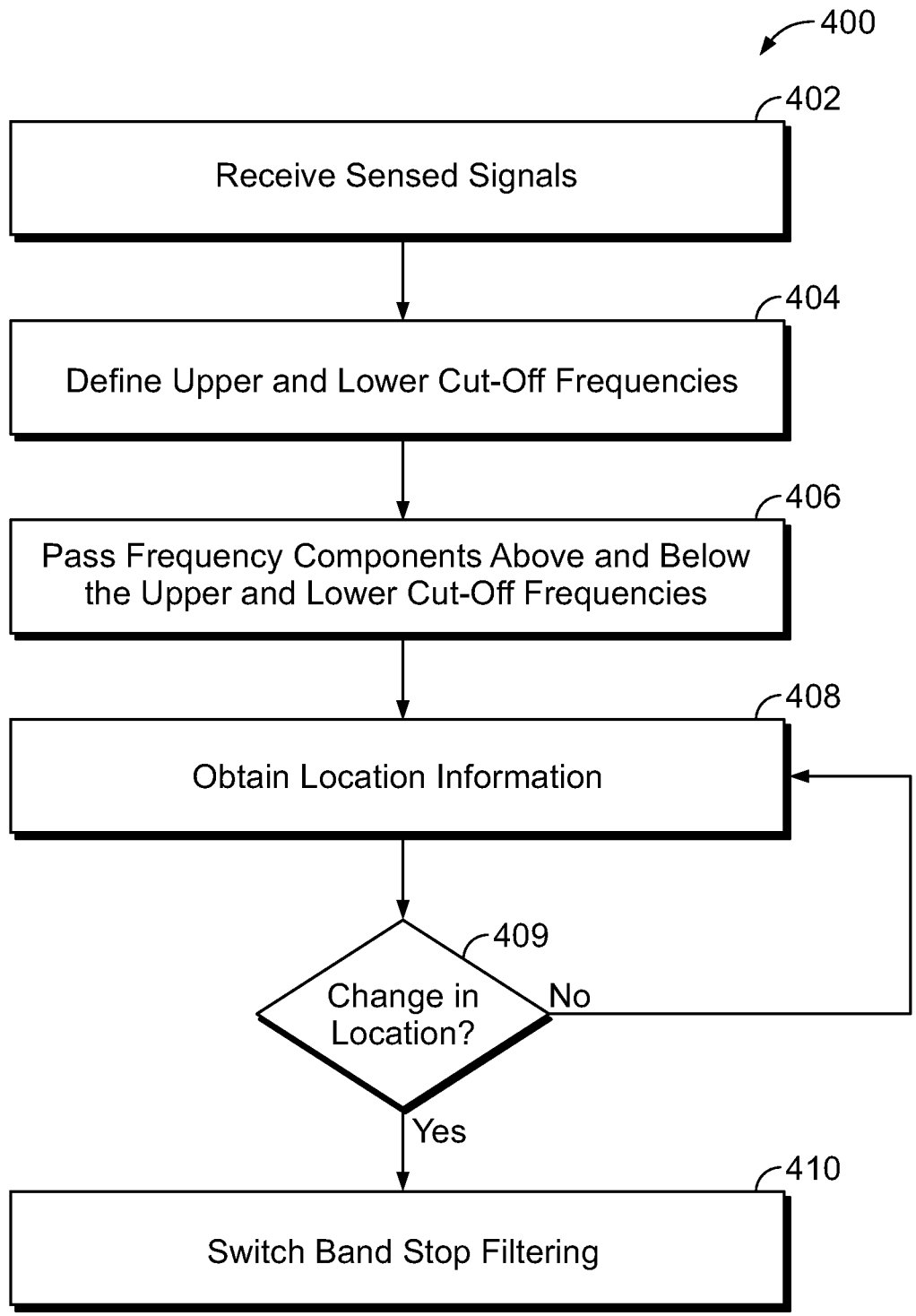
FIG. 4 illustrates a method of managing operations of an IMD, in accordance with embodiments herein.

FIG. 4 illustrates a method 400 for managing environmental based operations of an IMD in communication with an ED. All or a portion of the operations of FIG. 4 may be performed by one or more processors of the IMD, one or more processors of the ED, a server operating on a medical network, or the like.

At 402, one or more processors receive, at inputs of the IMD, sensed signals from one or more electrodes configured to be implanted. In one example, the IMD is the IMD described in relation to FIGS. 1-3B. The sensed signals from the one or more electrodes include electrocardiograph (ECG) signals. In particular, the sensed signals include frequency components associated with physiology activity and frequency components associated with noise. Specifically, for ECGs, the frequency content of the signal morphology is a function of temporal location within the cardiac cycle and whether abnormal conduction is present. The content of the P wave in one example is in a range of 5-30 Hz frequencies. The content of the QRS complex in an example contains a range of 8-50 Hz frequencies. Abnormal ventricular conduction in examples, includes higher frequencies, including above 70 Hz, forming notches on the QRS. Even though the majority of the frequency spectrum of normal non-arrhythmias are under 50 Hz, there are cases in which preserving the ECG to frequencies above 60 Hz is desired.

At 404, the one or more processors define upper and lower cut-off frequencies of a first noise stop band to filter noise that can be detected by the IMD. In one example the lower cut-off frequency is 45 Hz and the upper cut-off frequency is 55 Hz. Alternatively, the lower cut-off frequency is 55 Hz, and the upper cut-off frequency is 65 Hz. The first noise stop band in one embodiment is a default noise stop band that is initially provided by the IMD. The upper and lower cut-off frequencies can be determined based on the location of the implant of the IMD, patient location, distributor location, etc. Therefore, if the IMD is implanted in the U.S., the lower cut-off frequency can be 55 Hz and the upper cut-off frequency 65 Hz, whereas if the IMD is implanted in Europe, the lower cut-off is 45 Hz and the upper cut-off at 55 Hz.

Figure 5:
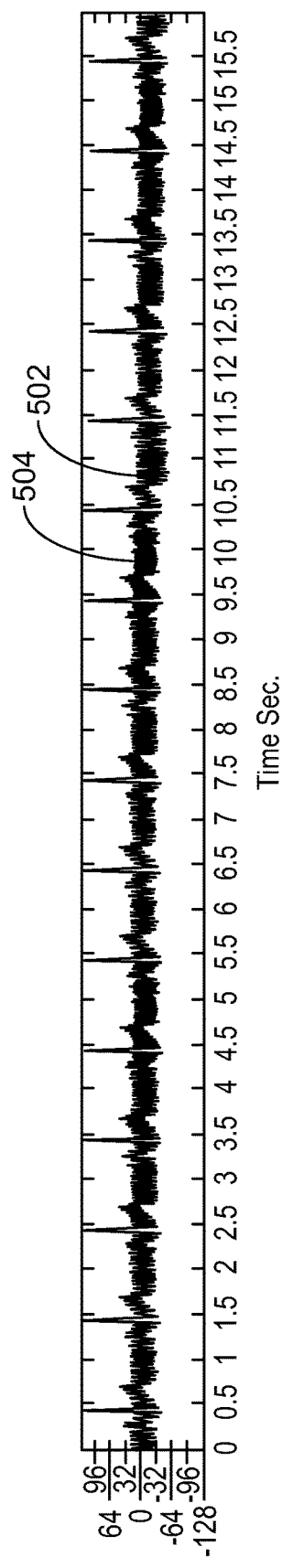
FIG. 5 illustrates a graph of an ECG signal, in accordance with embodiments herein.
Figure 6:
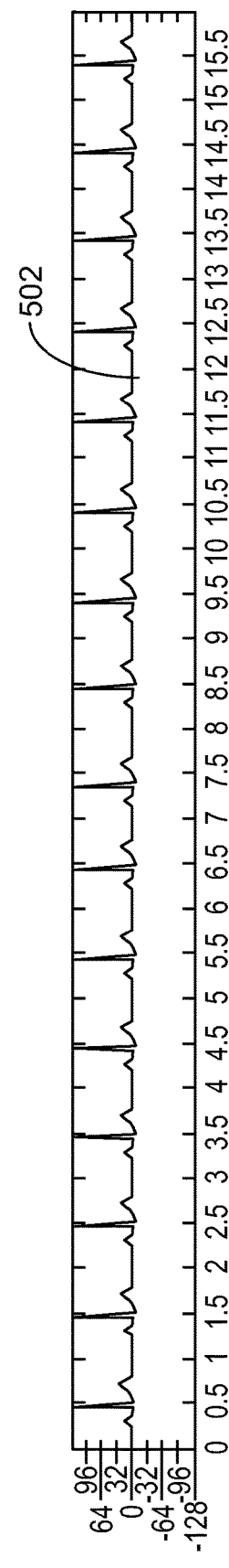
FIG. 6 illustrates a graph of an ECG signal, in accordance with embodiments herein.
Figure 7:
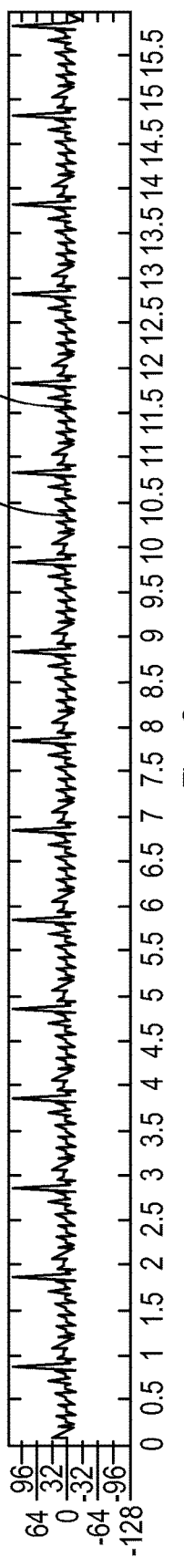
FIG. 7 illustrates a graph of an ECG signal, in accordance with embodiments herein.

When a patient is close to a high noise source, such as motors, a large amount of noise can be seen on the electrogram. FIG. 5 illustrates an ECG signal 502 that has a large amount of 50 Hz noise 504. FIG. 6 meanwhile shows the same ECG signal 502 of a patient in the same environment when applying a first order 50 Hz notch filter. As illustrated, the noise has been eliminated. Alternatively, FIG. 7 shows the same ECG signal 502 when a first order 60 Hz notch filter is applied, resulting in a waveform that still contains noise 504. As a result, the when the upper and lower cut-off frequencies are set, it is important to ensure the frequencies are within the frequency range of the expected noise.

At 406, the one or more processors pass the frequency components above and below the upper and lower cut-off frequencies associated with physiology activity, respectively, while at least partially blocking frequency components between the upper and lower cut-off frequencies associated with the noise to filter noise of the IMD. In this manner, the filter operates to filter noise within the upper and lower cut-off range to increase accuracy and precision of the IMD. As illustrated in FIGS. 5-7, the efficiency of the filtering depends upon, or is based upon, the upper and lower cut-off ranges.

At 408, the one or more processors obtain location information indicative of a location of at least one of the IMD or ED. The location information can be obtained using the internet of things (IoT), global navigation systems, mobile and cellular phones, Bluetooth beacon system, radio frequency identification, QR code identification, or the like.

In one example, the ED is a patient's smart watch that includes a GPS that may wirelessly communicates with an IMD. While visiting Japan, the patient begins a day in an area of Japan where power supplies are 50 Hz. Therefore, the smart watch wirelessly transmits an instruction to the IMD that the filter is to filter noise utilizing a parameter set with an upper cut-off frequency at 55 Hz and a lower cut-off frequency at 45 Hz. When the GPS of the smart watch detects that the patient has entered into a 60 Hz power supply region of Japan, the ED wirelessly transmits an FC instruction from the ED to the IMD to adjust the filter to begin filtering 60 Hz noise. Specifically, the first set of filter parameters switch from an upper cut-off frequency of 55 Hz and a lower cut-off frequency of 45 Hz to a second set of filter parameters with an upper cut-off frequency at 65 Hz and a lower cut-off frequency at 55 Hz.

In this manner, based on the location information the ED determines when the IMD has moved from a first location to a second location, and wirelessly transmits the FC instruction to the IMD based on the determining switching the first set of filter parameters to the second set of filter parameters. The ED wirelessly transmits the second set of filter parameters based on the location information, and in connection with the FC instruction that includes the second set of filter parameters, the filter is switched from the first set of filter parameters to the second set of filter parameters.

In another example, simultaneously with receiving the FC instruction, the first and second sets of filter parameters are stored in the memory of the IMD. The second set of filter parameters is then uploaded into registers of firmware of the IMD to shift to the second noise stop band. In this manner, the filter firmware may at a later time directly shift the first and second sets of filter parameters based on the stored filter parameters within the memory of the filter.

At 409, the one or more processors determine if the IMD has moved from a first location to a second location based on the obtained location information. If the IMD has not moved from a first location to a second location, the one or more processors continue to obtain location information. In particular, the first location and second location may both be defined by the type of electronic noise exists in a location. In this manner, the United States can be considered a first location and Europe a second location, because the standard frequency of electronics in the United States is 60 Hz, while in Europe the standard frequency of electronics is 50 Hz. In another embodiment, a mall area that includes electronic article surveillance (EAS) equipment that can emit magnetic frequencies between 10 Hz-1000 Hz. Specifically, EAS equipment, often used at shopping centers, creates artifacts that can cause problems for IMDs. So, if a particular mall area emits magnetic frequencies at 20 Hz, the mall area is may be considered a first location, and outside the boundaries of the mall area may be a second location. Similarly, a welding device at a patient's place of work may emit frequencies at 80 Hz such that the patient's place of work is a first location, and outside the patient's place of work is a second location. So, if a patient goes from their home to a restaurant where no change in potential noise is provided, the patient does not go from a first location to a second location. Instead, the patient is considered to remain in a first location during that entire time, even though the patient has moved.

If at 409, a patient moves from a first location to a second location, then at 410, the one or more processors switch band-stop filtering from a first set of filter parameters to a second set of filter parameters to change at least one of the upper and lower cut-off frequencies to shift from the first noise stop band to the second noise stop band. Specifically, based on the location of the IMD or ED, the upper and lower cut-off frequencies are defined and shifted to provide a different noise stop band.

Figure 8:
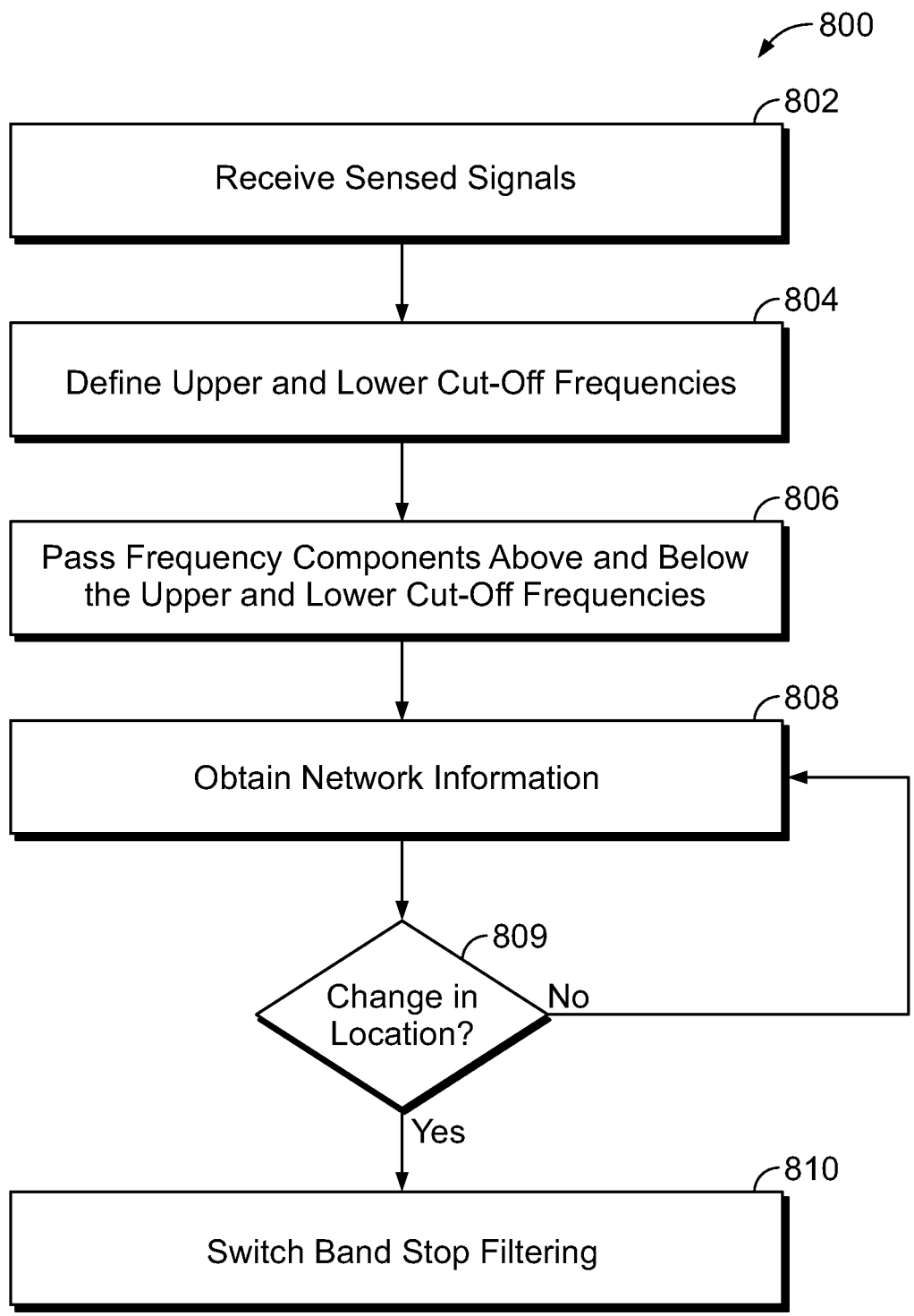
FIG. 8 illustrates a method of managing operations of an IMD in accordance with embodiments herein.

FIG. 8 illustrates a method 800 for managing environmental based operations of an IMD in communication with an ED. All or a portion of the operations of FIG. 8 may be performed by one or more processors of an IMD, one or more processors of an ED, a server operating on a medical network and the like.

At 802, one or more processors receive, at inputs of the IMD, sensed signals from one or more electrodes configured to be implanted. In one example, the IMD is the IMD described in relation to FIGS. 1-3B. The sensed signals from the one or more electrodes include ECG signals. In particular, the sensed signals include frequency components associated with physiology activity and frequency components associated with noise as described in relation to FIG. 4 and numeral 402.

At 804, the one or more processors define upper and lower cut-off frequencies of a first noise stop band to filter noise that can be detected by the IMD. In one example the lower cut-off frequency is 55 Hz and the upper cut-off frequency is 65 Hz. Alternatively, the lower cut-off frequency is 75 Hz, and the upper cut-off frequency is 105 Hz. The first noise stop band in one embodiment is a default noise stop band that is initially provided by the IMD. Alternatively, the sets of filter parameters are manually entered into an IMD or ED.

At 806, the one or more processors pass the frequency components above and below the upper and lower cut-off frequencies associated with physiology activity, respectively, while at least partially blocking frequency components between the upper and lower cut-off frequencies associated with the noise to filter noise of the IMD. In this manner, the filter operates to filter noise within the upper and lower cut-off range to increase accuracy and precision of the IMD.

At 808, the one or more processors obtain network information indicative of environmental noise. Specifically, the upper and lower cut-off frequencies can be determined based on the network that an ED is utilizing. In one example, if the ED determines that the ED has connected to a patient's home network within the U.S., the lower cut-off frequency can be 55 Hz and the upper cut-off frequency 65 Hz because the environmental noise of the electronics within the patient's home is 60 Hz. To this end, if the ED determines that the ED has connected to a patient's work network where the patient's work environment has welding equipment, the work network indicates environmental noise is 70 Hz based on the frequency of operation of the welding device. In another embodiment, if the ED has connected to a hospital network where magnetic resonance imaging (MRI), X-ray, and other medical equipment emits certain frequencies, the network information indicates environmental noise is 40 Hz. In yet another example embodiment, when the network is that of a shopping mall where EAS equipment is utilized, the shopping mall network indicates that a range of 20 Hz to 40 Hz is the environmental noise. Similarly, networks for office buildings, industrial plants, power plants, etc. may be utilized to determine specific noise within an environment.

At 809, the one or more processors determine if the IMD has moved from a first location to a second location based on the obtained network information. If the IMD has not moved from a first location to a second location, the one or more processors continue to obtain location information.

If at 809, a patient moves from a first location to a second location, then at 810, the one or more processors, switch band-stop filtering from a first set of filter parameters to a second set of filter parameters to change at least one of the upper and lower cut-off frequencies to shift from the first noise stop band to the second noise stop band. Specifically, based on the location of the IMD or ED, the upper and lower cut-off frequencies are defined and shifted to provide a different noise stop band.

In one embodiment, if the ED determines that the ED has moved from a first location to a second location by connecting to a home network within the U.S., the lower cut-off frequency can be 55 Hz and the upper cut-off frequency 65 Hz. Alternatively, if the ED determines that the ED has moved from a first location to a second location by connecting to a work network of a patient where welding equipment is utilized, the lower cut-off frequency may be 75 Hz and the upper cut-off frequency 85 Hz. In another embodiment, if the ED has moved from a first location to a second location by connecting to a hospital network where magnetic resonance imaging (MRI), X-ray, and other medical equipment emits certain frequencies, the lower cut-off frequency may be 35 Hz while the upper cut-off frequency may be 45 Hz. In yet another example embodiment, when the network is that of a shopping mall where EAS equipment is utilized, the lower cut-off frequency may be 20 Hz while the upper cut-off frequency may be 40 Hz. Therefore, by monitoring network changes within an ED or IMD indicative of the environmental noise of a patient, a first set of filter parameters may be switched to a second set of filter parameters.

Figure 9:
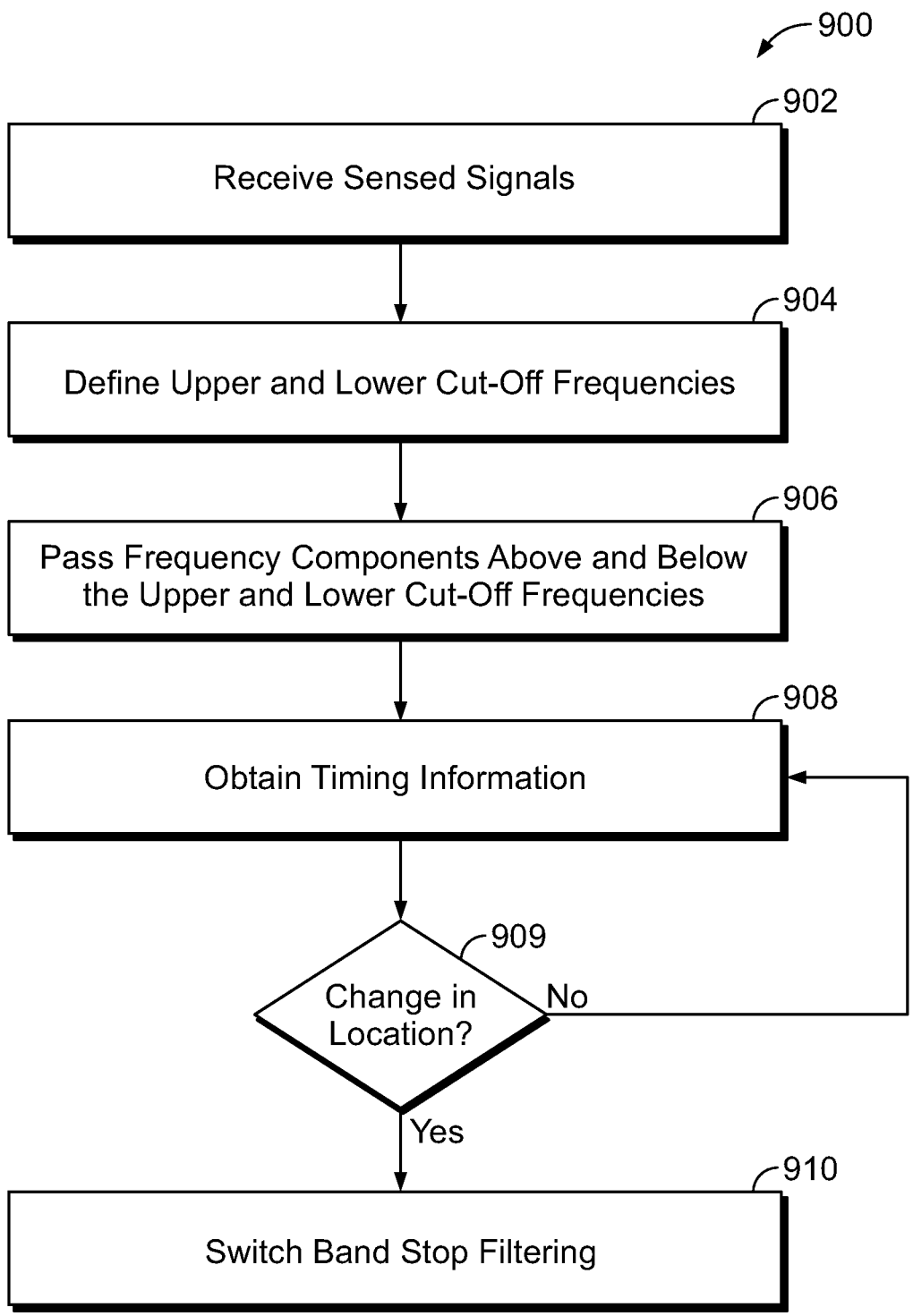
FIG. 9 illustrates a method of managing operations of an IMD in accordance with embodiments herein.

FIG. 9 illustrates yet another method 900 for managing environmental based operations of an IMD in communication with an ED. All or a portion of the operations of FIG. 9 may be performed by one or more processors of an IMD, one or more processors of an ED, a server operating on a medical network and the like. In this embodiment, time is utilized to determine changes in the noise in the environment of a patient.

At 902, one or more processors receive, at inputs of the IMD, sensed signals from one or more electrodes configured to be implanted. In one example, the IMD is the IMD described in relation to FIGS. 1-3B. The sensed signals from the one or more electrodes include ECG signals.

At 904, the one or more processors define upper and lower cut-off frequencies of a first noise stop band to filter noise that can be detected by the IMD. The first noise stop band in one embodiment is a default noise stop band that is initially provided by the IMD. Alternatively the upper and lower cut-off may be manually input into an ED or IMD.

At 906, the one or more processors pass the frequency components above and below the upper and lower cut-off frequencies associated with physiology activity, respectively, while at least partially blocking frequency components between the upper and lower cut-off frequencies associated with the noise to filter noise of the IMD. In this manner, the filter operates to filter noise within the upper and lower cut-off range to increase accuracy and precision of the IMD.

At 908, the one or more processors obtain scheduling or time based information indicative of environmental noise. Specifically, the upper and lower cut-off frequencies can be determined based on the time of the day, day of the week, time of the month, etc. For example, the IMD can include a programmed timing circuit based on a patient's work schedule and provides location information based on the time of day. According to the work schedule, the patient enters their work building Monday through Friday that includes a welding device at 7:00 AM. In this manner, a determination is made that the IMD has moved from a first location to a second location at 7:00 AM. Then, at 3:00 PM Monday through Friday, when the patient leaves work, again, a determination is made that the patient has moved from a first location (work) to a second location (outside of work) base on the time of day.

In another example, the ED may include a calendar that indicates when a patient is going to be on vacation, including the location of the vacation. The ED may utilize the calendar information to not utilize the timing circuit during that period because the patient will not be at work during that time. Additionally, if the vacation is in a location such as Europe that has different noise frequencies in their environment, the ED can provide a FC instruction at the time an airplane is scheduled to land in the European country at the beginning of the vacation. The ED can then provide a FC instruction at the time an airplane is scheduled to land back in the U.S. at the end of the vacation. Similarly, doctor appointments at a hospital or where MRI or other medical equipment is provided may obtained. The by utilizing a timing circuit, the ED may then switch the first set of filter parameters to a second set of filter parameters at the start time of an appointment to filter MRI generated noise, and switch the second set of filter parameters back to the first set of filter parameters a determined time, such as an hour, after the start of the appointment.

At 909, the one or more processors determine if the IMD has moved from a first location to a second location based on the obtained timing information. If the IMD has not moved from a first location to a second location, the one or more processors continue to obtain location information.

If at 909, a patient moves from a first location to a second location, then at 910, the one or more processors, switch band-stop filtering from a first set of filter parameters to a second set of filter parameters to change at least one of the upper and lower cut-off frequencies to shift from the first noise stop band to the second noise stop band. Specifically, based on the location of the IMD or ED, the upper and lower cut-off frequencies are defined and shifted to provide a different noise stop band. The timing circuitry can provide a FC instruction during determined time periods, such as the start and end of work, the start and end of a vacation, the start and end of an event such as an appointment, or the like, to switch the first set of filter parameters to the second set of filter parameters.

In yet another examples, other information is utilized to determine the environmental noise experienced by an IMD. In one such example, the IMD can include artificial intelligence AI that is coupled to an accelerometer associated with the IMD. The AI may monitor movements of the accelerometer related to a certain activity of the patient, such as using a welding device. In this manner, when certain repetitive movements of the patient occur, the IMD can determine the environment noise of the patient based on the movements. In this manner, the repetitive movements are considered information that is utilized to determine environmental noise.

Figure 10:
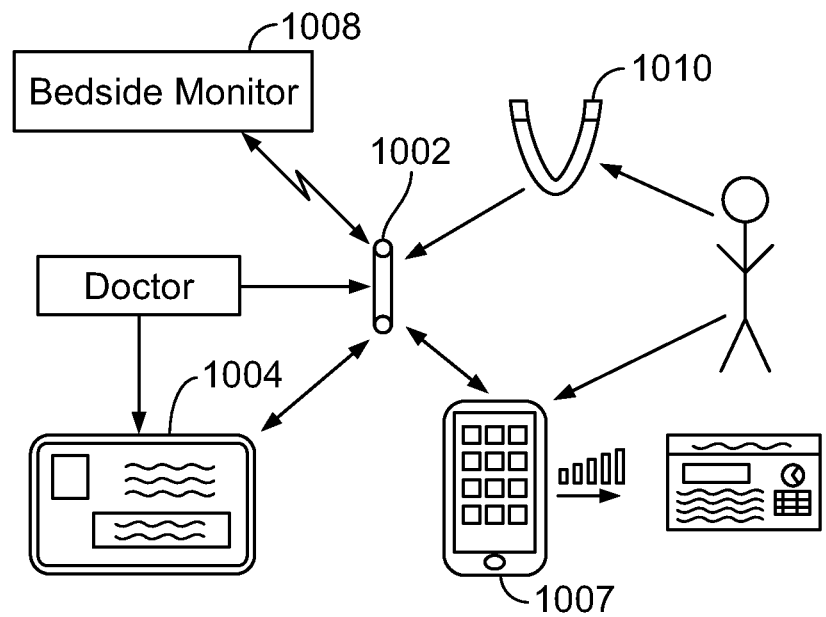
FIG. 10 illustrates a schematic block diagram of external devices (EDs) and networks in accordance with embodiments herein.

FIG. 10 illustrates a system level diagram indicating potential devices and networks that utilize the methods and systems herein. For example, an IMD 1002 (e.g., IMD 100 of FIG. 1) may be utilized to collect a cardiac activity (CA) data set that can be interfered with as a result of extrinsic noise in an environment. The IMD 1002 may supply the CA data set (CA signals, sensitivity levels, and motion data) to various local EDs, such as a tablet device 1004, a smart phone 1006, a bedside monitoring device 1008, a smart watch and the like. The devices 1004-1008 include a display to present the various types of the CA signals, markers, statistics, diagnostics, and other information described herein.

The IMD 1002 may convey the CA data set over various types of wireless communications links to the devices 1004, 1006 and 1008. The IMD 1002 may utilize various communications protocols and be activated in various manners, such as through a Bluetooth, Bluetooth low energy, Wi-Fi, or other wireless protocol. Additionally or alternatively, when a magnetic device 1010 is held next to the patient, the magnetic field from the device 1010 may activate the IMD 1002 to transmit the CA data set to one or more of the devices 1004-1008.

The processes described herein for managing environmental based operations may be implemented on or utilizing one or more of the devices 1004-1008. In particular, the devices 1004-1008 can include a GPS, determine network changes, include scheduling information and timers, etc. that can be utilized to determine the environment of the IMD, and provide FC instructions for an IMD.

Figure 11:
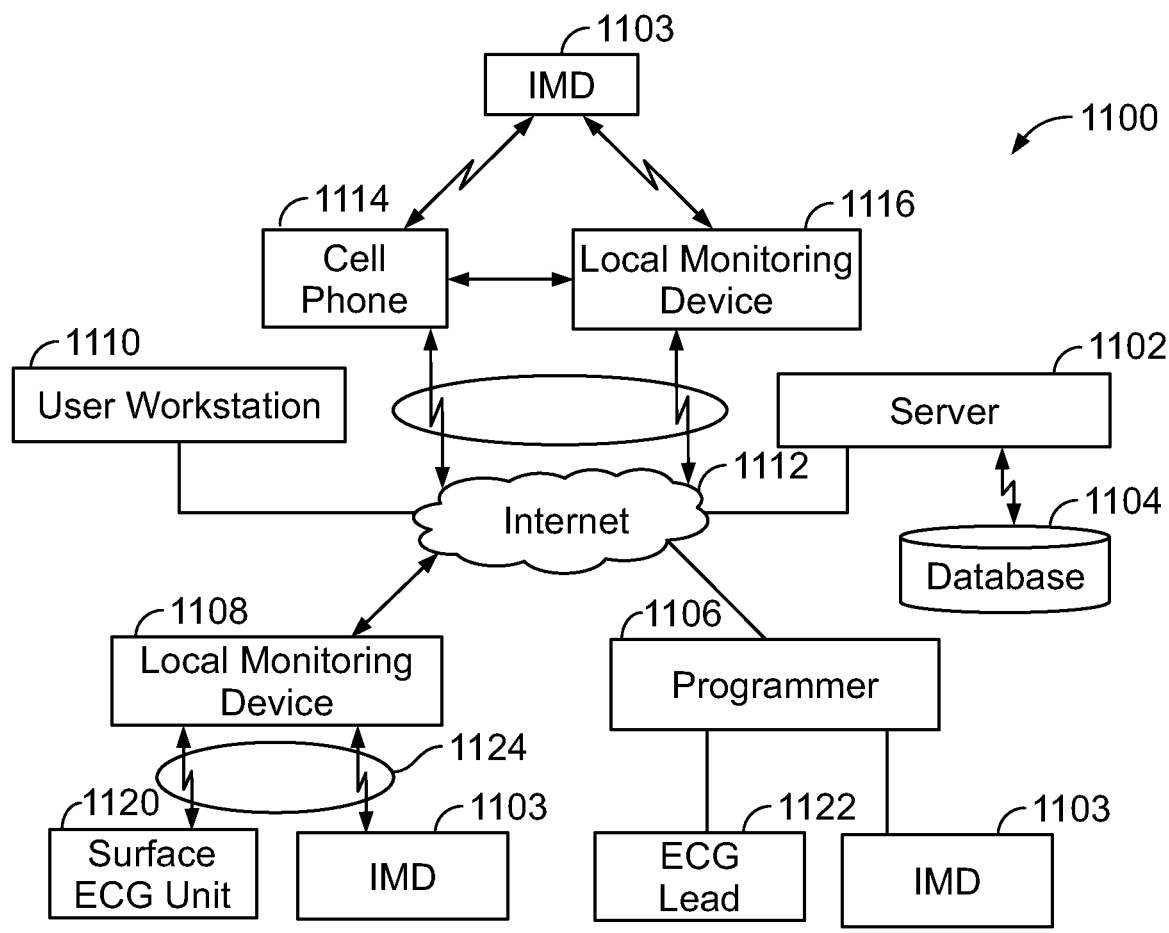
FIG. 11 illustrates a schematic block diagram of a distributed processing system in accordance with embodiments herein.

FIG. 11 illustrates a distributed processing system 1100 in accordance with embodiments herein. The distributed processing system 1100 includes a server 1102 connected to a database 1104, a programmer 1106, a local monitoring device 1108 (e.g., IMD 100) and a user workstation 1110 electrically connected to a network 1112. Any processor-based components (e.g., workstation 1110, cell phone 1114, local monitoring device 1116, server 1102, programmer 1106) may perform the processes discussed herein.

The network 1112 may provide cloud-based services over the internet, a voice over IP (VoIP) gateway, a local plain old telephone service (POTS), a public switched telephone network (PSTN), a cellular phone-based network, and the like. Alternatively, the communication system may be a local area network (LAN), a medical campus area network (CAN), a metropolitan area network (MAN), or a wide area network (WAM). The communication system serves to provide a network that facilitates the transfer/receipt of data and other information between local and remote devices (relative to a patient). The server 1102 is a computer system that provides services to the other computing devices on the network 1112. The server 1102 controls the communication of information such as CA signals, motion data, bradycardia episode information, asystole episode information, arrythmia episode information, markers, CA signal waveforms, heart rates, and device settings. The server 1102 interfaces with the network 1112 to transfer information between the programmer 1106, local monitoring devices 1108, 1116, user workstation 1110, cell phone 1114 and database 1104. The database 1104 stores information such as CA data, arrythmia episode information, arrythmia statistics, diagnostics, markers, CA signal waveforms, heart rates, device settings, and the like, for a patient population. The information is downloaded into the database 1104 via the server 1102 or, alternatively, the information is uploaded to the server 1102 from the database 1104. The programmer 1106 may reside in a patient's home, a hospital, or a physician's office. The programmer 1106 may wirelessly communicate with the IMD 1103 and utilize protocols, such as Bluetooth, GSM, infrared wireless LANs, HIPERLAN, 3G, satellite, as well as circuit and packet data protocols, and the like. Alternatively, a telemetry "wand" connection may be used to connect the programmer 1106 to the IMD 1103. The programmer 1106 is able to acquire ECG 1122 from surface electrodes on a person (e.g., ECGs), electrograms (e.g., EGM) signals from the IMD 1103, and/or CA data, arrythmia episode information, arrythmia statistics, diagnostics, markers, CA signal waveforms, atrial heart rates, device settings from the IMD 1103. The programmer 1106 interfaces with the network 1112, either via the internet, to upload the information acquired from the surface ECG unit 1120, or the IMD 1103 to the server 1102.

The local monitoring device 1108 interfaces with the communication system to upload to the server 1102 one or more of the CA signals, motion data, arrythmia episode information, arrythmia statistics, diagnostics, markers, CA signal waveforms, heart rates, sensitivity profile parameter settings and detection thresholds. In one embodiment, the surface ECG unit 1120 and the IMD 1103 have a bi-directional connection 1124 with the local RF monitoring device 1108 via a wireless connection. The local monitoring device 1108 is able to acquire CA signals from the surface of a person, CA data sets and other information from the IMD 1103, and/or CA signal waveforms, heart rates, and device settings from the IMD 1103, including after filtering of signals for environmental noise. On the other hand, the local monitoring device 1108 may download the data and information discussed herein from the database 1104 to the surface ECG unit 1120 or the IMD 1103.

The user workstation 1110 may be utilized by a physician or medical personnel to interface with the network 1112 to download CA signals, motion data, and other information discussed herein from the database 1104, from the local monitoring devices 1108, 1116, from the IMD 1103 or otherwise. Once downloaded, the user workstation 1110 may process the CA signals and motion data in accordance with one or more of the operations described above. The user workstation 1110 may upload/push settings (e.g., sensitivity profile parameter settings), IMD instructions, other information, and notifications to the cell phone 1114, local monitoring devices 1108, 1116, programmer 1106, server 1102 and/or IMD 1103.

The processes described herein in connection managing environmental based operations may be performed by one or more of the devices illustrated in FIG. 11, including but not limited to the IMD 1103, programmer 1106, local monitoring devices 1108, 1116, user workstation 1110, cell phone 1114, and server 1102. The process described herein may be distributed between the devices of FIG. 11.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices, and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system comprising:
    one or more electrodes configured to be implanted proximate to a sensing site;
    memory configured to store first and second sets of filter parameters that define first and second noise stop bands;
    an implantable medical device (IMD) configured to be implanted within a patient, comprising:
        inputs configured to receive sensed heart signals from the one or more electrodes, the sensed heart signals include frequency components associated with physiology activity related to the sensed heart signals and frequency components associated with noise;
        a band-stop filter communicating with the inputs, the band-stop filter including an independently selectable low-pass filter that provides the first noise stop band and an independently selectable high-pass filter that provides the second noise stop band;
        the band-stop filter utilizing the first set of filter parameters to define upper and lower cut-off frequencies of the first noise stop band, the band-stop filter configured to pass the frequency components above and below the upper and lower cut-off frequencies associated with physiology activity, respectively, while at least partially block frequency components between the upper and lower cut-off frequencies associated with the noise;
        memory to store program instructions;
        a processor that, when executing the program instructions, is configured to:
            at least one of analyze the sensed heart signals or deliver a therapy;
            determine a noise in an environment of the patient; and
            independently switch the band-stop filter from the low-pass filter to the high-pass filter or the high-pass filter to the low-pass filter to change at least one of the upper and lower cut-off frequencies to shift from the first noise stop band to the second noise stop band based on the noise in the environment of the patient to detect the sensed heart signals.

2. The system of claim 1, further comprising an external device (ED) located external of the patient when the IMD is implanted in the patient, wherein the processor is configured to wirelessly receive a filter change (FC) instruction from the external device, and in response to the FC instruction, the processor configured to manage the band-stop filter to independently switch from the low-pass filter to the high-pass filter or the high-pass filter to the low-pass filter.

3. The system of claim 2, wherein the ED comprises an ED transceiver, an ED processor and memory configured to store ED program instructions, the ED processor, when executing the ED program instructions, configured to determine a location of the external device and, based on the location, to determine when to independently switch between the low-pass filter and the high-pass filter or the high-pass filter to the low-pass filter, the ED transceiver configured to wirelessly transmit the FC instruction to the IMD based on the determination.

4. The system of claim 2, wherein the ED is one of a workstation, a portable computer, an IMD programmer, a personal digital assistant (PDA), a phone, or a watch.

5. The system of claim 1, wherein the processor is further configured to wirelessly receive the second set of filter parameters and, in connection there with, independently switch from the low-pass filter to the high-pass filter or the high-pass filter to the low-pass filter.

6. The system of claim 1, wherein the band-stop filter is implemented in firmware having registers configured to hold a current one of the first and second sets of filter parameters to define the upper and lower cut-off frequencies, the memory configured to simultaneously store both the first and second sets of filter parameters, the band-stop filter configured to upload the second set of filter parameters into the registers of the firmware to shift to the second noise stop band.

7. The system of claim 1, wherein the memory further comprises software that defines the band-stop filter, the processor configured to implement the software utilizing one of the first and second sets of filter parameters.

8. The system of claim 1, wherein the upper and lower cut-off frequencies are the same.

9. The system of claim 1, wherein the upper cut-off frequency is in a range between 45 Hz and 75 Hz and the lower cut-off frequency is in a range between 45 Hz and 75 Hz.

10. The system of claim 1, wherein the band-stop filter is a digital filter is configured to function as a first order filter and as a second order filter based on coefficient values of the digital filter, and to independently switch the band-stop filter from the low-pass filter to the high-pass filter when the coefficient values are changed.

11. The system of claim 1, wherein the processor is further configured to select one of the low-pass filter or the high-pass filter based on the noise in the environment of the patient.

12. A system comprising:
one or more electrodes configured to be implanted proximate to a sensing site;
memory configured to store first and second sets of filter parameters that define first and second noise stop bands;
an implantable medical device (IMD), comprising:
inputs configured to receive sensed heart signals from the one or more electrodes, the sensed heart signals include frequency components associated with physiology activity related to the sensed heart signals and frequency components associated with noise;
a band-stop filter communicating with the inputs, the band-stop filter including an independently selectable low-pass filter that provides the first noise stop band and a high-pass filter that provides the second noise stop band; the band-stop filter utilizing the first set of filter parameters to define upper and lower cut-off frequencies of the first noise stop band, the band-stop filter configured to pass the frequency components above and below the upper and lower cut-off frequencies associated with physiology activity, respectively, while at least partially block frequency components between the upper and lower cut-off frequencies associated with the noise;
memory to store program instructions;
a processor that, when executing the program instructions, is configured to:
at least one of analyze the sensed heart signals or deliver a therapy;
obtain location information indicative of a location of the IMD; and
based on the location information, independently switch the band-stop filtering from the low-pass filter to the high-pass filter or the high-pass filter to the low-pass filter to detect the sensed heart signals.

13. The system of claim 12, wherein the location information is obtained by an external device (ED) that is in communication with the IMD, the processor further configured to wirelessly receive a filter change (FC) instruction from the ED to the IMD, and in response to the FC instruction, the IMD independently switching from the low-pass filter to the high-pass filter or the high-pass filter to the low-pass filter.

14. The system of claim 13, wherein based on the location information, the processor is further configured to determine when the location of the IMD has moved from a first location to a second location.

15. The system of claim 13, wherein the processor is further configured to wirelessly receive the second set of filter parameters from the ED to the IMD, based on the location information and, in connection there with, independently switch from the low-pass filter to the high-pass filter or the high-pass filter to the low-pass filter.

16. The system of claim 12, wherein the processor is further configured to simultaneously store both the first and second sets of filter parameters in the memory of the IMD; and upload the second set of filter parameters into registers of firmware of the IMD to shift to the second noise stop band.

17. The system of claim 12, wherein the processor is further configured to monitor movement from a first location to a second location; and
wherein to independently switch the band-stop filtering from the low-pass filter to the high-pass filter or the high-pass filter to the low-pass filter to change at least one of the upper and lower cut-off frequencies to shift from the first noise stop band to the second noise stop band is based on the movement from the first location to the second location.

18. The system of claim 17, wherein the first set of filter parameters are in a range between 45 Hz and 55 Hz at the first location, and the second set of filter parameters are in a range between 55 Hz and 65 Hz at the second location.

19. The system of claim 12, wherein to obtain location information indicative of a location of the IMD comprises obtaining a signal from a global positioning system of an external device (ED) in communication with the IMD.

20. The system of claim 12, wherein to independently switch the band-stop filtering from the low-pass filter to the high-pass filter or the high-pass filter to the low-pass filter based on the location of the IMD being where electronic article surveillance equipment is present.

* * * * *